United States Patent [19]
Barbour et al.

[11] Patent Number: 5,137,355
[45] Date of Patent: Aug. 11, 1992

[54] METHOD OF IMAGING A RANDOM MEDIUM

[75] Inventors: Randall L. Barbour, Westbury; Jack Lubowsky, Merrick; Raphael Aronson, Great Neck, all of N.Y.

[73] Assignee: The Research Foundation of State University of New York, Albany, N.Y.

[21] Appl. No.: 363,075

[22] Filed: Jun. 8, 1989

Related U.S. Application Data

[63] Continuation-in-part of Ser. No. 204,101, Jun. 8, 1988.

[51] Int. Cl.$^5$ ............................................. G01N 21/00
[52] U.S. Cl. ................................... 356/342; 128/664; 356/237
[58] Field of Search ............... 356/342, 237; 128/633, 128/664, 665; 250/358.1

[56] References Cited

U.S. PATENT DOCUMENTS

| 4,555,179 | 11/1985 | Langerholc et al. | 356/237 |
| 4,810,875 | 3/1989 | Wyatt | 250/227.11 |
| 4,829,184 | 5/1989 | Nelson et al. | 250/358.1 |

OTHER PUBLICATIONS

Langerholc, J. "Moving Phase Transitions in Laser-Irradiated Biological Tissue" *Applied Optics* vol. 18, No. 13 (Jul. 1, 1979).

Primary Examiner—Richard A. Rosenberger
Attorney, Agent, or Firm—Morgan & Finnegan

[57] ABSTRACT

A non-invasive medical imaging technique capable of evaluating, in situ, the oxygenation state of body tissues (e.g., by measuring the spectral properties of heme proteins) is described. The technique is based on the measurement of scattered radiation in the near-infrared region (NIR), where significant penetration into body tissues occurs. The disclosed technique employs a multi-wavelength collimated source and a collimated receiver and performs a positional and angular scan of the scattered radiation for each position of the incident beam. The resultant data is evaluated by employing imaging schemes which give differential weights to the contribution of various volume elements (voxels) in the medium to the detector response. A three-dimensional spectroscopic image of the target medium is determined by considering the contribution of the various volume elements for each source-detector configuration and position of the incident beam at various frequencies. These measurements, in an imaging mode, yield vital physiological information while being, for example, a sensitive indicator of subtle physiological stress caused by disease or trauma.

23 Claims, 7 Drawing Sheets

1. MEASURE INTENSITY OF EMERGING RADIATION AT DESIRED FREQUENCIES.

2. APPLY MEASURED INTENSITY SIGNAL TO DATE PROCESSING SCHEME.

3. DATA PROCESSING SCHEME.

A. DETERMINE ATTENUATION OF EMERGING RADIATION OF TARGET MEDIUM RELATIVE TO MODEL MEDIUM.

B. DETERMINE RELATIVE CONTRIBUTION OF VOXEL ELEMENTS FOR EACH SOURCE-DETECTOR CONFIGURATION.

C. SUPERIMPOSE RELATIVE CONTRIBUTION OF VOXEL ELEMENTS FOR ALL SOURCE - DETECTOR CONFIGURATIONS.

D. REPEAT DATA PROCESSING STEPS FOR ALL DESIRED FREQUENCIES TO OBTAIN SPECTROSCOPIC IMAGE.

4. DISPLAY 3-DIMENSIONAL SPECTROSCOPIC IMAGE

METHOD OF IMAGING A RANDOM MEDIUM

CROSS REFERENCE TO RELATED APPLICATIONS

This application is a continuation-in-part of co-pending application Ser. No. 07/204,101, filed on Jun. 8, 1988.

FIELD OF THE INVENTION

This invention pertains to the detection and three-dimensional imaging of absorbing and/or scattering structures in complex random media by detecting scattered radiation emerging from the medium.

BACKGROUND OF THE INVENTION

The detection and identification of objects within a turbid medium has long challenged investigators from diverse technical disciplines. For example, at visible frequencies objects or vessels located in fog are rendered largely undetectable, thus inhibiting safe navigation. In material science methods have long been sought to remotely image faults or other inhomogenieties within optically transluscent or opaque materials.

Objects buried in a random medium are rendered optically invisible because of the effects of scattering. Scattering causes light to experience multiple paths thereby obscuring phase information.

In a general sense the detection or imaging of subsurface objects in a random medium requires the solution of an inverse problem. Specifically this requires an understanding of how the medium affects the propagation of light. Mathematically this can be described by a modulation transfer function.

While prior art techniques have allowed observers to detect the presence of an object within a turbid medium (see below), none have allowed the observer to detect its depth or structure. In clinical medicine, for example, it would be useful to detect the presence, size, location, and depth of a suspected tumor.

In particular, it would be especially desirable to perform such measurements in a manner which could also monitor the close association between oxidative metabolism and organ function. As described below, this relationship can be determined by measuring the oxygenation or redox-state of heme proteins in situ (e.g. hemoglobin, myoglobin, cytochrome oxidase) using optical transmission or reflectance techniques.

An optical technique which could differentiate depth-of-field may be used to generate a 3-Dimensional image of body tissues which identifies the oxygenation state of those tissues. Such measurements would thus permit the 3-D imaging of the functional activity of the tissue. Indeed, the development of such a technique would be useful for other applications including detecting and imaging objects located within the atmosphere or, in oceanographic studies for the imaging of submerged vessels or other subsurface objects.

Because of the strong scattering properties of tissues, it is often not practical to study their optical properties by a transmission measurement. On the other hand, by resorting to a reflectance or backscatter measurement the spectroscopic properties of tissue can be studied.

Much interest in this technique has been generated in recent years because of its ability to monitor, in a continuous and non-invasive fashion, in situ, the oxygenation state of heme proteins. Such measurements are highly desirable because of the well established relationship between oxygen availability, oxidative metabolism and organ function.

Using reflectance techniques, the effects that hypoxic hypoxemia, hypercapnia, carbon monoxide, and cyanide induced hypoxemia have on cerebral and cardiac energetics can be monitored and compared to simultaneous measurements of organ function.

Such studies demonstrate the extreme sensitivity of organ energetics and function to minimal changes in tissue oxygen levels as measured by the oxygenation state of heme proteins. The latter findings are consistent with results obtained using phosphorus NMR. Recent clinical investigations employing NIR reflectance measurements have demonstrated that rapid changes in brain oxygenation, blood volume and energy state occurred in response to hyperoxia, moderate hypoxia and hypercapnia. These investigations emphasize the clinical usefulness of this technique.

Although it has been recognized that optical studies of tissue (particularly in the reflectance mode) can potentially yield highly significant and useful information regarding organ function, such measurements are of little clinical value without the ability to characterize some degree of depth-of-field.

In fact, depth-of-field differentiation is critical. Without a depth-of-field differentiation these techniques cannot even distinguish between a superficial bruise on the scalp and a more serious internal injury.

The inability to differentiate depth-of-field in tissue by past optical measurement techniques has compelled the prior art to restrict measurements to the identification of the overall oxygenation state of the tissue (i.e., solely one dimensional information). For example, U.S. Pat. No. 4,281,645 (Jobsis) discloses a spectrophotometric transillumination method for non-invasive monitoring of the metabolism of a body organ which performs this type of one-dimensional measurement. Jobsis also discussed this prior art technique in *Reflectance Spectrophotometry and Non-Invasive, Infrared Monitoring of Cerebral and Myocardial Oxygen Sufficiency and Circulatory Parameters* (1977). Such spectrophotometric techniques are not able to use the dispersion pattern generated by objects buried in the target medium to image the objects and establish their location within the surrounding target medium.

Prior attempts have been made to locate and image objects located within a turbid medium by utilizing transillumination techniques, for example, diaphanography, where light is directed towards a target object. In transillumination the target object is detected by shadows in the light pattern emerging at the opposite side of the medium.

Typical of such prior attempts include inventions disclosed by United Kingdom Patent Application Nos. 2,068,537A, 2,111,794, 2,154,731, and 2,092,856 and U.S. Pat. No. 4,312,357. Such transillumination techniques only permit an observer to determine the two-dimensional outline of the target object. Thus its depth within the surrounding tissue and its three-dimensional structure remain unknown. Furthermore, these transillumination techniques require that a specimen be relatively thin and that both sides of the specimen be accessible to the measurement device.

U.S. Pat. No. 4,555,179 (Langerholc et. al.) discloses a method and apparatus for the detection of objects in a scattering medium. The Langerholc technique employs a collimated light source which scans the medium. The reflected radiation is then analyzed to detect the presence of the target object. If the absorption characteristics of the target object were previously known, the observer could determine the object's depth within the medium. For clinical studies, such information can not be practically obtained.

A further serious drawback of the Langerholc method is that, in practice, the method described can only locate objects relatively close to the surface of the medium being scanned. In addition, unlike the current invention, the measurement described involves integrating the backscattered signal over an area having a diameter equal to 2.5 times the thickness of the medium (i.e. the so-called "scattering zone"). This restriction renders such an approach useless for measurement of targets having limited geometries, i.e. the human body. Furthermore, by integrating over this area, specific information regarding variations in the position and angle dependent emerging flux is lost.

On the other hand, the present invention recognizes the significance of performing a position and angle scan of the scattered light as essential in identifying regional variations in the absorptive and scattering properties of a turbid medium. Indeed, discussions of techniques such as Langerholc's admit that they are only able to detect objects along one dimension. These include wires or blood vessels. This is of limited value when the observer wishes to know the location, size, and shape of three-dimensional objects within a turbid medium.

Bonner et al., in *Model For Photon Micration in Turbid Biological Medium* (1987), recognized that analysis of positional information can be used to infer sub-surface properties of a random medium. However, Bonner does not disclose how such information may be used to generate an image of the target medium.

While prior art techniques have allowed observers to detect the presence of an object within a turbid medium, none have allowed the observer to image its depth or structure. In many medical and other applications, such information is vital.

The present invention describes an imaging technique which may be used to study the brain and breast. The presence of tumors, cysts, hypoxic or infracted regions will be readily detectable. For obstetrical procedures, it will be possible to image the oxygenation state of an unborn fetus's brain, in utero, just prior to delivery. The progression of atherosclerosis on the delivery and utilization of oxygen by tissues (in particular, limbs) could be directly assessed. Because the technique of the invention is noninvasive and nondestructive and yields vital physiological information, it will also be useful in monitoring the response of body tissues to various therapies. In particular, the technique of the present invention may be used to monitor and evaluate the physiological status of burned patients, immuno-compromised patients or other patients restricted to isolation rooms.

The inventive technique represents an accurate and reliable means to assess the functioning of transplanted organs as well as being a sensitive means to detect, in situ, impending organ rejection. The disclosed technique wil be helpful in monitoring the physiological status of excised donor organs for impending recipient implantation. Its use during anesthesia will permit, for the first time, direct in situ monitoring of the delivery to and utilization of oxygen by the brain. Such measurements in a hospital emergency room setting with unconscious patients would differentiate accurately and rapidly between patients suffering from carbon monoxide-, cyanide-, or other drug poisonings which interfere with oxygen utilization from patients having suffered a stroke or subtle cerebral trauma.

Studies in marine environments using visible and/or near infrared (NIR) sources will permit the remote monitoring of the oxygenation status of plants and animals, in situ. Such measurements will indicate the physiological impact of environmental pollutants. Other marine studies may involve the imaging of turbulence at increasing ocean depths. The proposed method may also be used in search and rescue operations for the imaging of objects or victims buried in snow, ice or muddy waters.

In a general sense, the above applications pertain to the imaging of objects which exist in the medium at the time of measurement. The present technique may also permit the determination of events which have previously occurred and thereby affected changes in the environment. This is particularly useful for the measurement of affects on marine life.

Commercial applications of the proposed technique include the remote inspection of food products for spoilage or contamination by insecticides. As a remote imaging method, the proposed technique might aid aircraft or naval navigation in foggy atmospheres. Other commercial applications include the monitoring of various processes involved in the production of bulk industrial commodities at critical steps involving significant hazards to operators. The remote imaging of optically opaque objects which are not readily explored by a transmission measurement may also be imaged. Examples include the interrogation of low fault tolerant components of existing structures for the detection of fault lines or other fractures by the use of x-ray or particle beam sources. These may include nuclear reactor shielding, hulls of commercial or military aircraft, etc.

Consequently, it is an object of this invention to provide a method for allowing an observer to accurately detect, three-dimensionally image and spectroscopically characterize target objects located within a turbid medium.

Another object of the present invention is to employ radiation directed towards target objects located in a random medium and to detect radiation scattered from the medium to enable the observer to determine the object's depth, structure, absorptive and scattering properties within the turbid medium.

A further object of this invention is to image reference objects in a non-invasive and non-destructive manner.

Yet another object of the present invention is to provide a method whereby a physician may use the invention to aid in medical diagnosis.

For example, a goal of this invention would be to measure the oxygenation state of body tissues and to display this information as a three-dimensional image to yield vital physiological information while still being a sensitive indicator of subtle physiological stress caused by disease or trauma.

Additional objects and advantages of the invention will be set forth, in part, in the following description, will be obvious, in part, from this description, or may be learned from the practice of this invention. The objects and advantages of the invention are realized and obtained by the processes and methods particularly pointed out in the following description and claims.

SUMMARY OF THE INVENTION

These and other objects are accomplished by the present invention which provides a method for detecting and imaging an object having different absorptive or scattering properties than that of its surrounding turbid medium.

The inventive technique directs radiation into a medium towards a suspected target or reference object located within the medium. The directed radiation may be multiple frequencies and may be generated by C.W. or ultra-fast pulse sources, (e.g. for time-of-flight studies). The invention recognizes that the analysis of position and angle dependence of scattered radiation inherently yields information which may be used for imaging; in particular, for the generation of three-dimensional images.

In one aspect of the invention, by using reflectance spectrophotometric techniques, reflectance data from the reference object is analyzed.

An aspect of the invention is the recognition that by directing a collimated beam of radiation into a turbid medium, radiation can be identified which has propagated to successively increasing depths in the medium. This may be done by measuring positional dependent flux which emerges from the medium at increasing distances from the radiation source.

Positional dependent measurements may include measuring the angular dependence of emerging flux at increasing distance from the source. This off-axis measurement yields a "depth profile" of objects and other optical inhomogenieties within the medium.

The invention recognizes that lateral detection, at greater distances from the incident source than previously contemplated, is a key to providing necessary imaging information. Whereas radiation back-scattered to a detector positioned laterally close to the incident beam is largely unable to detect deeply buried objects, such objects can be detected by receptors positioned at greater distance from the source.

The invention uses data measured by a collimated receiver or receiver array which is directed towards the medium and located about the radiation source. The receiver array and light source are directed to multiple locations about the surface, thereby effecting a two-dimensional surface scan.

Another aspect of the invention relates to the analysis of positional and angular dependent emerging flux. This data allows the recreation of a three-dimensional image of the medium.

The invention recognizes that reflectance spectrophotometric data, processed correctly, inherently yields data which may be used for imaging. This is based on an observation that radiation undergoing multiple scattering at increasing depths within a turbid medium (such as living tissue) will emerge at increasing distance from the source.

The invention recognizes that the proper analysis of data may involve a differential weighting of the targeted medium with each weighting function corresponding to a particular source detector configuration. This differential weighting affords differential depth information regarding the scattering and absorptive properties of the medium.

The invention allows the determination of the relative contribution of various volume elements within the medium to the detector response. Reconstruction of a three-dimensional image may be accomplished by the superposition of the relative contribution of each volume element, (i.e. voxel) to the detector response for each source-detector configuration.

The invention may be utilized for various medical and non-medical applications.

Therefore, in accordance with the present invention, a method for imaging a three dimensional object in a turbid medium is provided. The method comprises:

A method for imaging a three-dimensional target object or other optical inhomogeniety in a turbid medium, comprising the steps of:

providing a substantially collimated beam of radiation and directing the beam onto a surface of a turbid medium containing a target object;

providing a substantially collimated receiver to receive the scattered radiation;

performing positional scans of the scattered radiation over the surface of the turbid medium;

applying the data obtained from each positional scan to form a three-dimensional image of the target object by:

a. determining attenuation of emerging radiation from said target medium relative to a model medium;

b. determining a relative contribution of volume elements for each source-detector configuration;

c. superimposing the relative contribution of volume elements for all source-detector configurations;

d. repeating the above steps a to c for all desired frequencies to obtain a spectroscopic image.

Another important aspect of the novel technique is to perform a positional and angular scan of the radiation backscattered from the turbid medium wherein the target object is located. The technique employs a collimated light source and either a moveable collimated detector or a detector array, which permits the detection of a positional-dependent angular flux. The more differential the available information, the more which can be inferred about the properties of the backscattering medium. Moving the source relative to the detector yields additional information.

BRIEF DESCRIPTION OF THE DRAWINGS

The invention will be described in greater detail hereinafter by way of reference to the following drawings.

DETAILED DESCRIPTION OF THE PREFERRED EMBODIMENT

The measurement and analysis routine of the present invention may be readily applied to the imaging of any scattering medium. The inventive technique involves inherently remote imaging which may be directed to not only living tissue, but oceans, atmospheres or other turbid media.

The radiation employed by the invention is not restricted to visual radiation, but may be radiation of much higher or much lower wavelength including the entire spectral range and other types of radiation, e.g., x-ray, audible radiation or wavelengths used in radar.

An aspect of the invention introduces a method for imaging a three-dimensional target object o other optical inhomogeniety in a turbid medium, comprising the steps of:

providing a substantially collimated beam of radiation and directing the beam onto a surface of a turbid medium containing a target object;

providing a substantially collimated receiver to receive the scattered radiation;

performing positional scans of the scattered radiation over the entire surface of the turbid medium;

applying the data obtained from each positional scan to form a three-dimensional image of the target object by:

a. determining attenuation of emerging radiation from said target medium relative to a model medium;

b. determining a relative contribution of volume elements for each source-detector configuration;

c. superimposing the relative contribution of volume elements for all source-detector configurations;

d. repeating the above steps a to c for all desired frequencies to obtain a spectroscopic image.

The inventor has recently characterized the three dimensional dispersion of light in a random medium of isotropic scatterers with a buried absorber using a Monte Carlo simulation routine. These results, described below, serve to illustrate the importance of considering positional and angular dependent emerging flux as a means to selectively interrogate increasing depths in a random medium.

Figure 1:
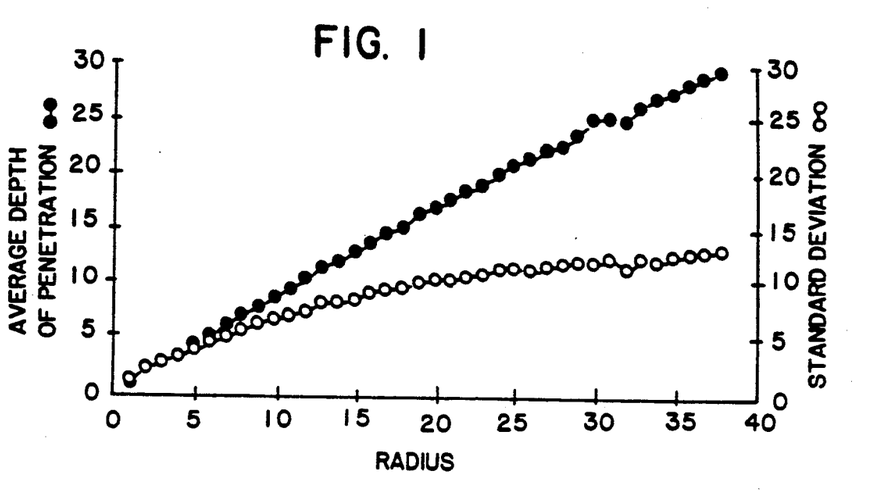
FIG. 1 is a graph illustrating the average maximum depth of penetration of emerging light as a function of radial distance from the source.

The mean value ± standard deviation (expressed in terms of mean free paths (mfp) of the average maximum depth to which the emerging light penetrates) are shown in FIG. 1 as a function of radial distance from the source. Here, the simulation involved launching one million photons from a point collimated source and allowing each photon to undergo up to 20,000 collisions. The mean free path was equal to unity.

The dispersion of photons in such a medium as described by FIG. 1 is simulated by generating three random numbers from a pseudo-random number generator. These numbers represent the angles $\theta$(theta), and $\phi$(phi), and the distance R. $\theta$ is the angle between the vector represented by a scattered photon and the Z axis. $\phi$ is the angle between the x axis and the vector sum of the x and y components of the vector represented by the scattered photon. R is the free path length of the photon to the next collision within the dispersive medium.

Each time a new scattering vector is to be computed for a photon within the medium three new random numbers are needed; one each for $\theta$, $\phi$ and R. The random number generator produces a number between 0 and 1. The uniform scattering model assumes that photons uniformly scattered from the center of a unit sphere must produce a uniform density of photons that reemerge from the surface of the sphere. Phi must therefore be uniformly distributed between 0 and $2\pi$ radians (360 degrees). A random number, n, from the random number generator will have a value uniformly distributed between 0 and 1. Multiplied by $2*\pi$. This will result in a random number with an equal probability of falling anywhere within the range of 0 to $2\pi$ This is used for the value of $\phi$.

Theta must be distributed between 0 and $\pi$ such that its cosine has an equal probability of falling anywhere within the range of $-1$ to $+1$. Accordingly, $$\cos \theta = 1 - 2*n \tag{1}$$

The free path R is distributed according to:

$$P(L) = \frac{1}{L_m} e^{-\frac{L}{L_m}} \tag{2}$$

where $L_m$ is the mean free path for the medium.

Given random number n, set $$L = L_m * \text{Log} \frac{1}{1-n} \tag{3}$$

Equation (3) will yield a random variable L distributed as specified by the function P(L) in equation (2).

There is a near linear relationship between the average maximum depth of penetration of the emerging light and the distance from the source. Thus, light emerging farther from the source has preferentially penetrated to a greater depth than light emerging near the source.

Figure 2:
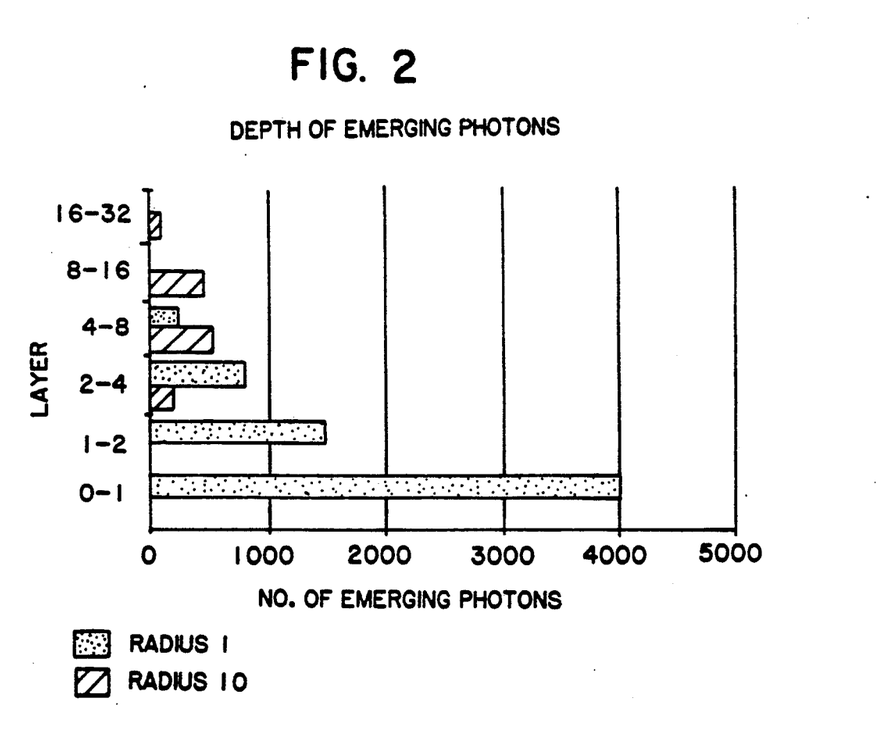
FIG. 2 is a graph illustrating the depth distribution of emerging photons at different distances from the source as a function of maximum depth of penetration of emerging.

The fraction of incident photons which have propagated to their maximum depth prior to emerging at a distance of 1 and 10 mfP from the source as a function of maximum depth of penetration is shown in FIG. 2. This fraction was determined by standard Monte Carlo techniques. At a distance of 1 mfp from the source, approximately 60% of the emerging light has penetrated to a maximum depth of between 0–1 mfp into the medium followed by an exponential decline at greater maximum depths. In contrast, at a distance of 10 mfp from the source, most of the emerging light has propagated to a maximum depth of 4–8 mfp into the medium. The conditions of the simulation were the same as described in FIG. 1.

Figure 3:
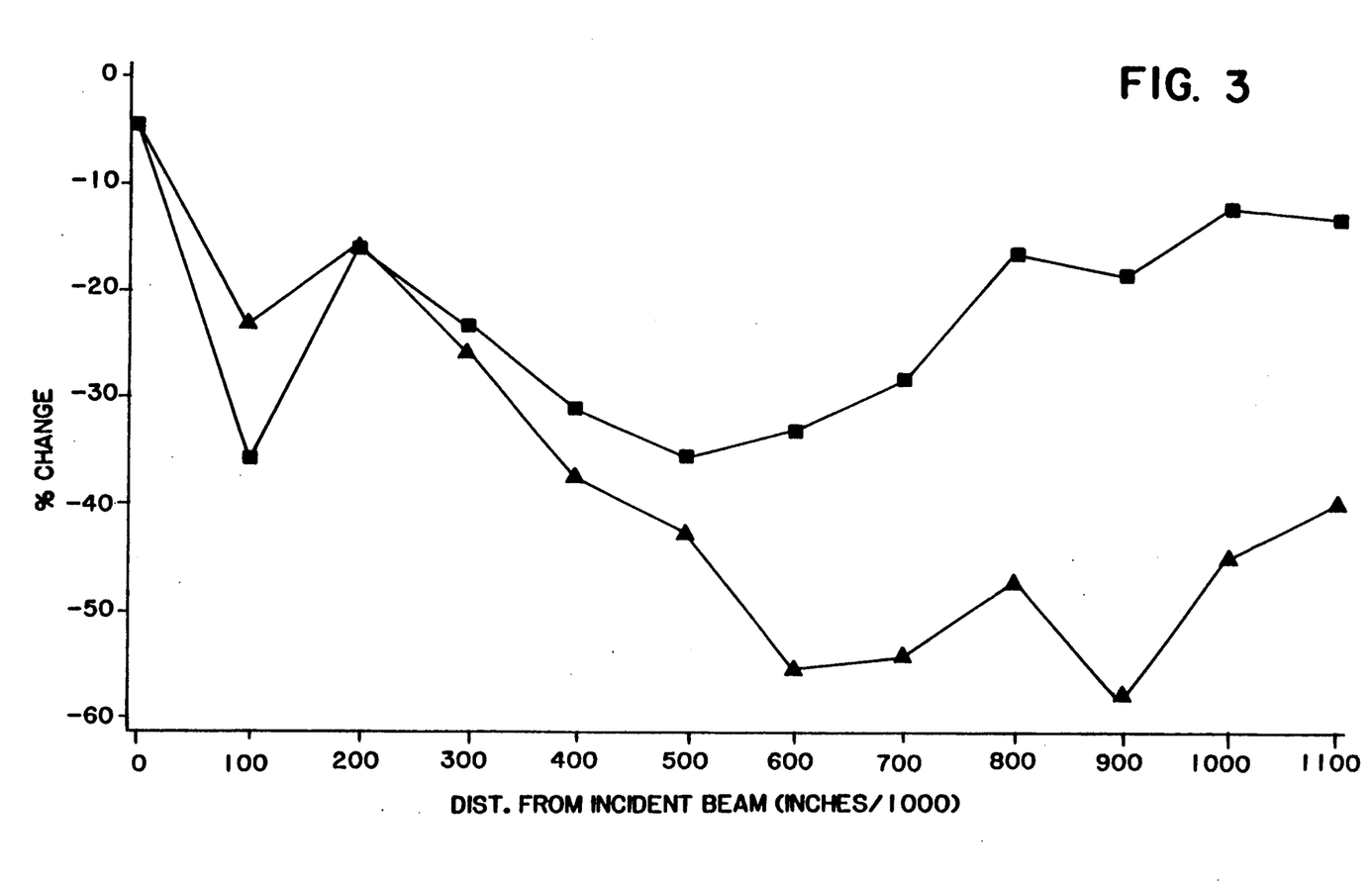
FIG. 3 is a graph illustrating the reduction in light intensity at increasing distances from the source in a multilayer agar medium.

Experimental results shown in FIG. 3 show the relative intensity of backscattered light, at increasing distances from the source of multilayer turbid agar media with biological absorbers, compared to an agar medium with no absorbers.

The medium with no absorbers was prepared by adding microscopic uniform latex beads (0.202 um diameter) to liquified clear agar and allowed to gel, forming a 6 mm thick layer. Agar medium containing latex beads and intact, heat treated red blood cells was similarly prepared. The intensity of backscattered light was then measured for the agar medium containing three layers of no absorbers and compared to agar media having a middle layer of intact red blood cells and a middle and bottom layer of intact, heat treated red blood cells respectively.

The turbidity of the top agar layer rendered the lower absorbing layers undetectable to the eye when viewed in room light. However, as shown in FIG. 3, these layers become increasingly detectable when measured by a collimated source (He-Ne laser) and a collimated receiver positioned laterally at increasing distances from the source.

Figure 4:
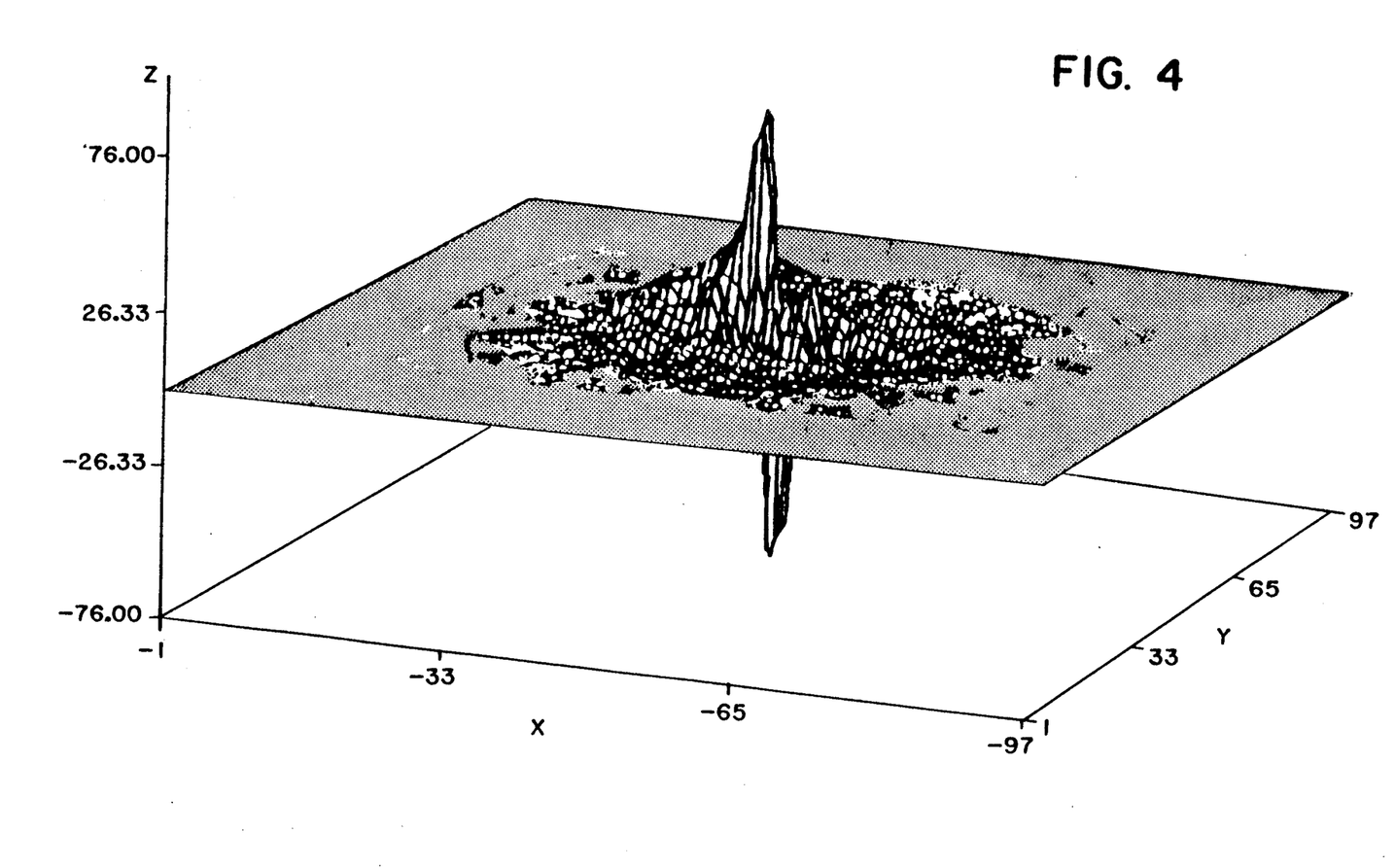
FIG. 4 is a graph illustrating a radial difference plot of the effect of a buried absorber on the intensity of emerging light from a Monte Carlo calculation.

Further evidence substantiating the merits of an off-axis measurement are shown in FIG. 4. Therein, results show a Monte Carlo calculation demonstrating the effect of a buried absorber on the intensity of emerging light as displayed by a radial difference plot. This simulation involved launching of 1 million photons from a point collimated source at coordinates 50,50 with each photon undergoing a maximum of 400 collisions. Photons emerging through an acceptance angle of 120°–150° with respect to the direction of launching were detected at each point along the surface of 100×100 mfp grid. The absorber formed a 2×2×2 mfp cube and was positioned 8 mfp from the source and 4 mfp below the surface. The plot shown in FIG. 4 was smoothed by calculating the moving average over a 3×3 mfp. area. It is apparent that the impact of the buried absorber is best seen by evaluating intensity data at increasing distances from the source.

Figure 5:
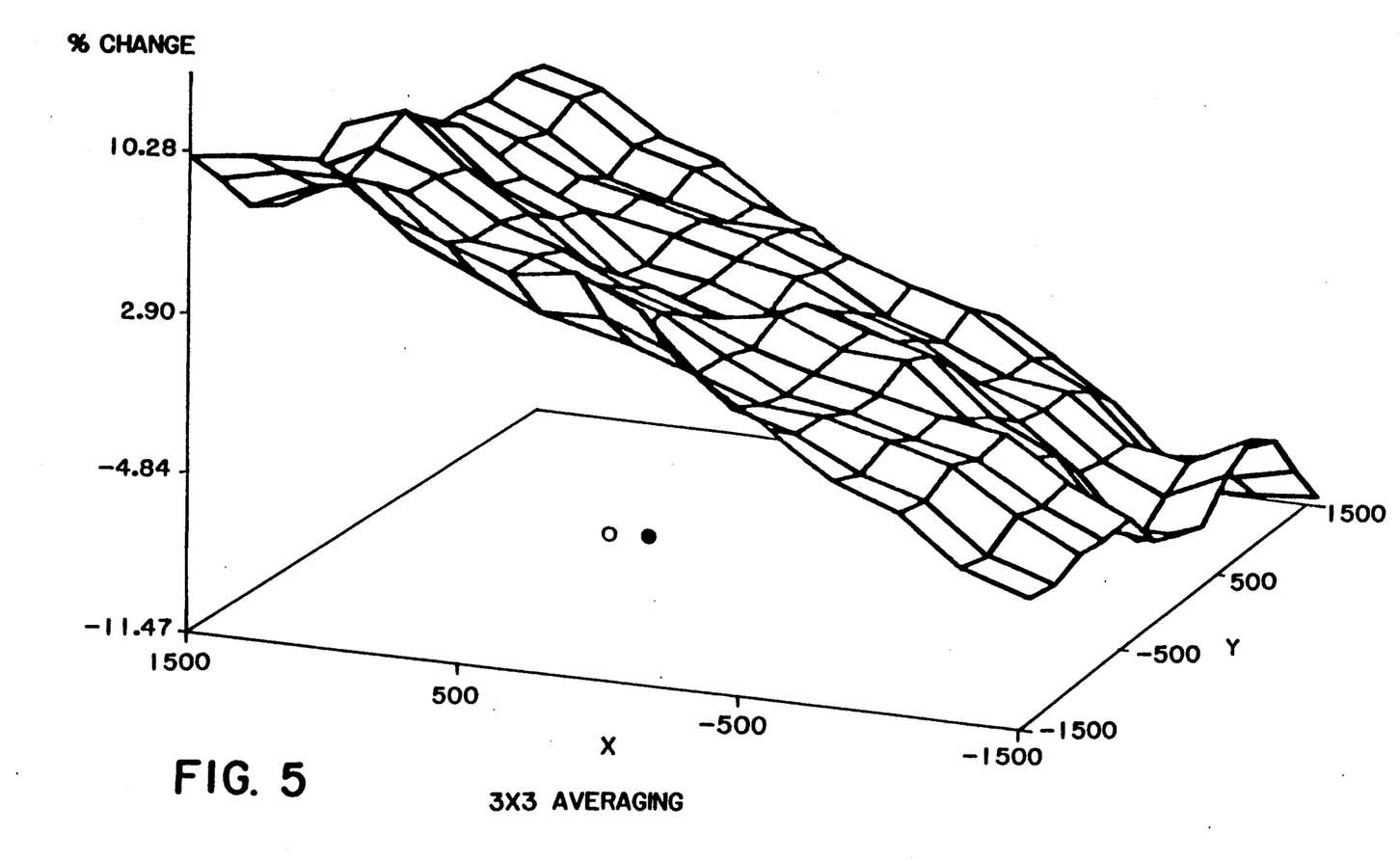
FIG. 5 is a graph illustrating a radial difference plot of the effect of a buried absorber on the intensity of emerging light from experimental results.

A corresponding evaluation of experimental results demonstrating the effect of a buried absorber on the intensity of emerging light as displayed by a radial difference plot is shown in FIG. 5. A two dimensional surface scan was performed using a collimated receiver tilted 30° from normal.

In FIG. 5, Z-coordinate values correspond to the intensity difference, in percent, between one side of the source and its radial opposite. Values for x and y axis are indicated in thousandths of an inch from the source. The medium consisted of uniform latex beads (0.202 um diameter) in water in which a black plastic bead (0.1" diameter) was suspended at a depth (0.75") sufficient to render it undetectable from the surface when viewed in room light.

The lateral displacement of the absorber from the source is indicated by the open circle. The solid circle indicates the x, y coordinates of the calculated "center-of-mass" of the intensity differences on one-half of the plain. Analysis of the change in position of the calculated "center-of-mass" for several beam positions correctly determined the position of the absorber to within 10% of its actual location.

The invention provides a unique technique for imaging complex media by initially assigning to every point (locations and direction) in the medium a weight given by the product of the flux (direct solution) and the expected contribution of a photon at the point to the detector response (adjoint or backward solution) for the medium without the absorber.

If the absorption is small, the effect of an absorber at that point is proportional to the weight. The effect of all the absorbers is a linear combination of such contributions. When the absorption is not small, the effect is no longer linear, but the linear combination will serve as a first approximation. To obtain the weight functions, one must compute both the direct and adjoint fluxes, or alternatively, directly compute the contribution flux.

Determination of these weight functions for specified media are relatively straightforward, although for unknown heterogeneous media such as body tissues the solution is more complex (see below). However, the anatomy of the body is well defined. Large veins near the surface are readily apparent and the location of other major arteries and veins deep within tissues are also well known. In the context of an imaging scheme, these major components of the vascular tree can viewed as optical landmarks which would aid in the calibration of the weighing functions.

Clearly, the more accurately the contribution of various regions of tissues can be assigned to the detected signal, the greater the image resolution and spectroscopic accuracy. The detection of these optical landmarks together with the measurement of angular dependence of emerging flux (as a function of distance from source and position of source relative to the media) will provide differential information concerning the optical properties of tissues. The more such differential information is available, the more detailed the inferrences about the properties of the medium which can be made. A time-to-flight analysis could also be performed in conjunction with the weight function.

In a simple consideration of the weight functions, one might decide that when the weights are normalized to run from 0 to 100, an absorber at any point with a weight of less than 5 cannot be detected. One keeps only the volume within this contour and assumes that any detectable absorber must lie inside. A given source-detector reading is observed relative to the reading expected without an absorber. Any absorber must lie in the corresponding volume. The absorber, if any, must then lie in the volume complementary to the union of all of these excluded volumes.

This incremental exclusion process provides an image of the absorber. For absorbers near the surface the image is sharp, because of the contribution by single scattering. However, the resolution will degrade for succeeding depths. One may repeat this procedure continually, excluding volumes outside the contour surface of weight 10, 20 or 50. Of course, each tightening of the acceptable volume tightens any image obtained at the possible expense of missing it altogether.

In its preferred embodiment, the device of the present invention would detect light scattered from an optical inhomogeneity, such as a tumor, located within an optically dispersive medium such as normal human tissue. The incident radiation in this embodiment would be near infrared (NIR) light with a wavelength of 750–1000 nm.

The instrumentation of the present invention, in a preferred embodiment, is controlled by a microcomputer and have, as major components, an NIR tunable dye laser, a precision linear translator having 5 degrees of freedom, two NIR-sensitive photomultiplier tubes, phase-locked amplifiers and electronic components to detect the light signal.

Functionally, the instrument operates similar to a double-beam scanning spectrophotometer. A beam splitter will direct a portion of the incident light from the dye laser to an NIR-sensitive PMT (reference signal), while the remaining light will be directed to the sample. Scattered light will then be detected by a second NIR-sensitive PMT housed within a collimator (sample signal).

The latter device may be attached to an overhead precision linear translator having 5 degrees of freedom of movement (x, y, z, phi, theta). Signals from the two PMT's will then be directed to the amplifiers and the signal ratio determined. The intensity of the laser, its output wavelength, positioning of the linear translators, and acquisition and storage of the measured light signal may be controlled by a microcomputer.

While the above discussion has emphasized the ability to image variations in the absorptive properties of random media, the technique is equally capable of imaging variations in the intensity of backscattered light caused by differences in the scattering cross section of the medium unrelated to its absorptive properties. Differentiation between these two effects can be made by examining the spectroscopic properties of the medium, i.e., comparing results at different wavelengths.

In a second preferred embodiment of the invention, a measurement scheme employs a source of collimated radiation in the near-infrared region (NIR) of the spectrum.

The source directs radiation towards a target medium (i.e., body tissue). Radiation propagating through the medium will experience multiple scattering prior to emerging.

A collimated receiver or receiver array detects the emerging radiation. The receiver array may be translated to perform a position and angle scan of the radiation. These scans are performed about the collimated source which is also translated.

The present invention characterizes the relative contribution of emerging flux from each volume element in the medium. The characterization considers the depth of the volume element and distance and angle of the receiver from the source. As described below, the technique relates the information obtained from actual measurements of positional dependent flux to determine the relative contribution of each volume element to the detector response. This information is used to reconstruct a 3-dimensional image.

In the shown preferred embodiments, the geometry of the source-detector configuration is arranged to perform a reflectance (i.e., backscatter) measurement. However, additional embodiments are envisioned in which the geometry of the source/detector configuration allows transmission and other measurement schemes to be performed.

In another preferred embodiment the source may utilize either a continuous or ultra-fast pulse laser which may operate at various frequencies. The use of ultra-fast sources with a streak-camera as a receiver allows time-of-flight measurements of intensity. The analysis of time-of-flight data is similar to that for a continuous source. However, the advantage of the time-of-flight measurement would be to reduce the volume of medium contributing most to the detector response, thereby yielding a higher resolution image.

Figure 6:
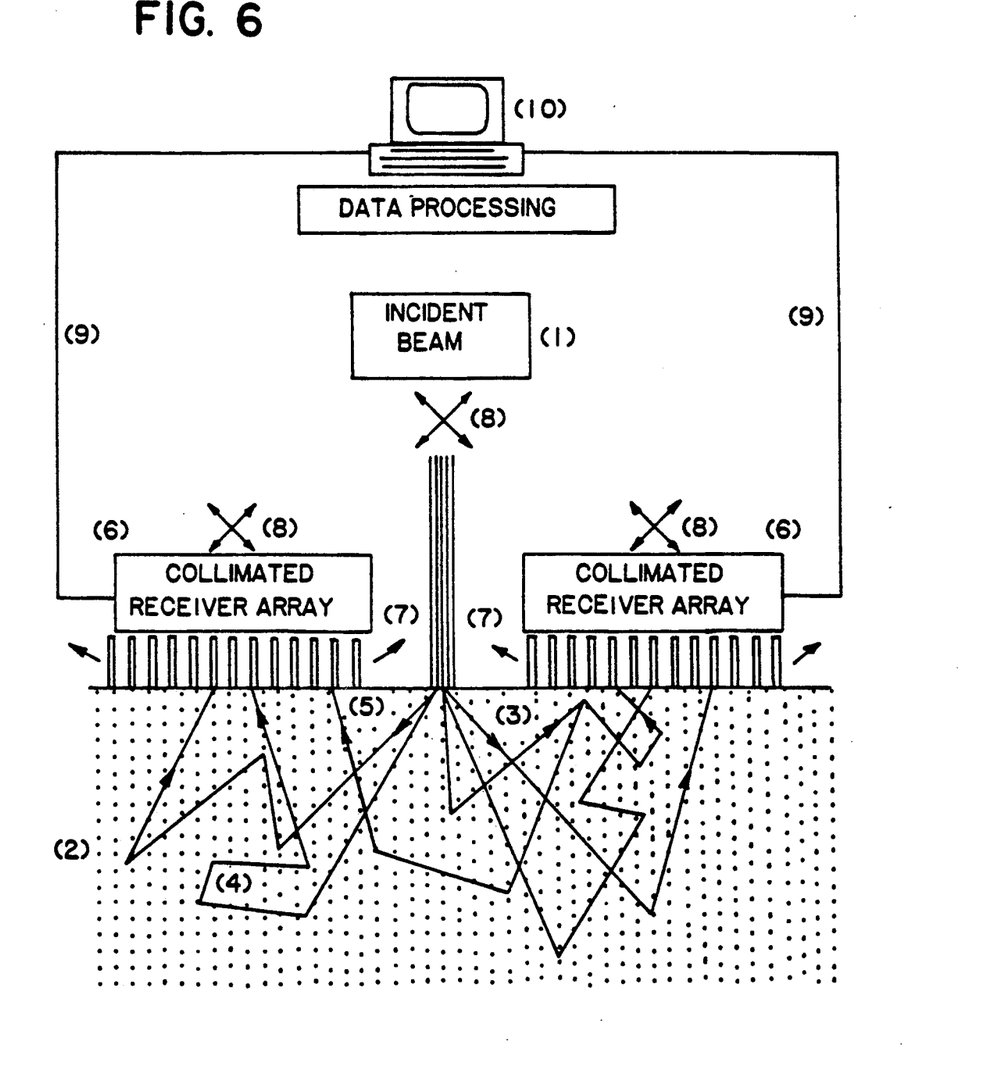
FIG. 6 is an abbreviated illustration of the interaction of the technique of the present invention with a turbid medium.

FIG. 6 depicts the interaction of the technique of another preferred embodiment with a random turbid medium. A collimated incident beam of radiation is directed towards a turbid medium 2. In this preferred embodiment incident beam 1 may be a multifrequency source in the near infrared (NIR) region of the spectrum. This is preferred for spectroscopic studies of body tissues because at these frequencies light is known to penetrate deeply into the tissue medium. Additionally, a multifrequency measurement can be utilized to identify the relative oxygenation state of heme proteins.

Radiation propagating through the medium 3 experiences multiple collisions 4 prior to emerging from the medium 2.

Emerging radiation 5 will be detected by a collimated receiver array 6 positioned about the source 1 thereby effecting a surface scan. The angle of the receiver 6 relative to the source 1 may also be varied 7.

Both the source 1 and receiver array 6 may also be translated about the surface 8 in order to perform an overall surface scan and thereby greatly improve subsequent image resolution.

The source 1 and the receiver array 6 are collimated, and caused to undergo their respective surface and angular scans to enhance subsequent image resolution.

In this preferred embodiment of the invention, receiver arrays 6 are positioned about the source 1 to reduce scanning time. However, other embodiments are envisioned which engage either a single collimated receiver as described above or a single receiver array which performs multiple scans. Additionally, in a further embodiment of the invention multiple sources may be utilized to mimic the translation of a single source.

In this preferred embodiment, the receiver array 6 may be caused to contact the medium's surface or may be position at a distance from the target medium 2 when detecting emerging radiation 5. In one embodiment of the invention the receiver arrays are cooled CCD elements, however the receiver may be any type of radiation intensity detection mechanism. The detected radiation intensity is transformed into an electrical signal and transmitted 9 to a data processing unit 10. The data processing unit 10 transforms the radiation intensity signal into a 3-dimensional image of the target medium.

Figure 7A:
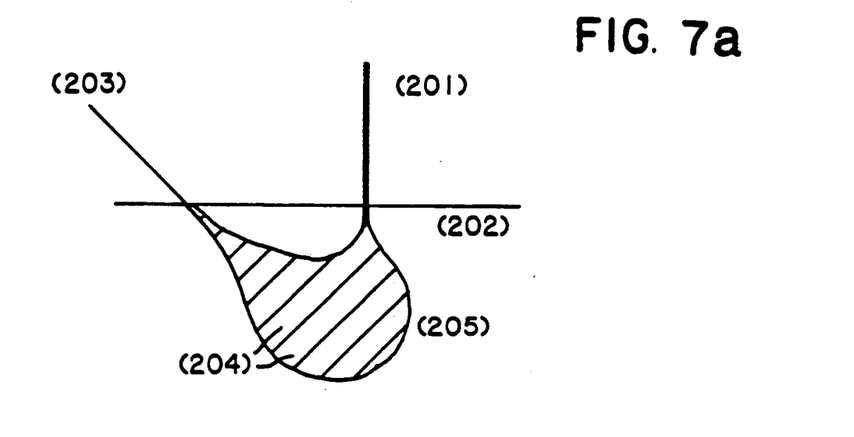
FIG. 7A is an abbreviated illustrative rendition of the contour of a relative weight function level utilized by the method of the preferred embodiment of the invention.
Figure 7B:
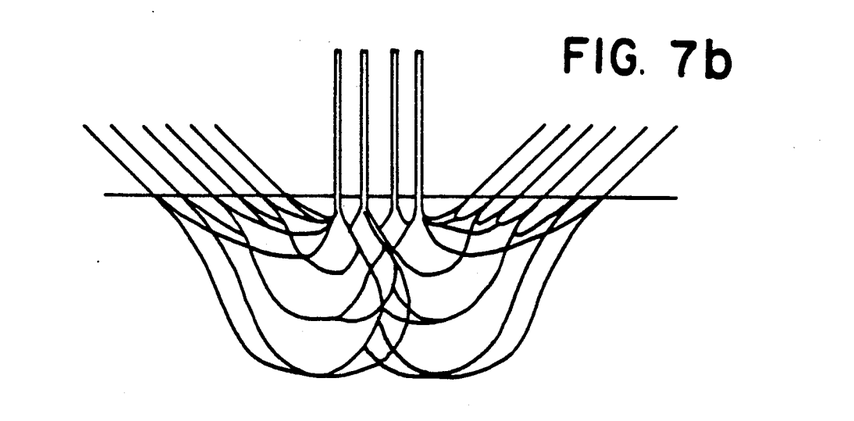
FIG. 7B is an abbreviated rendition of the superposition of the contour of FIG. 7A.
Figure 7C:
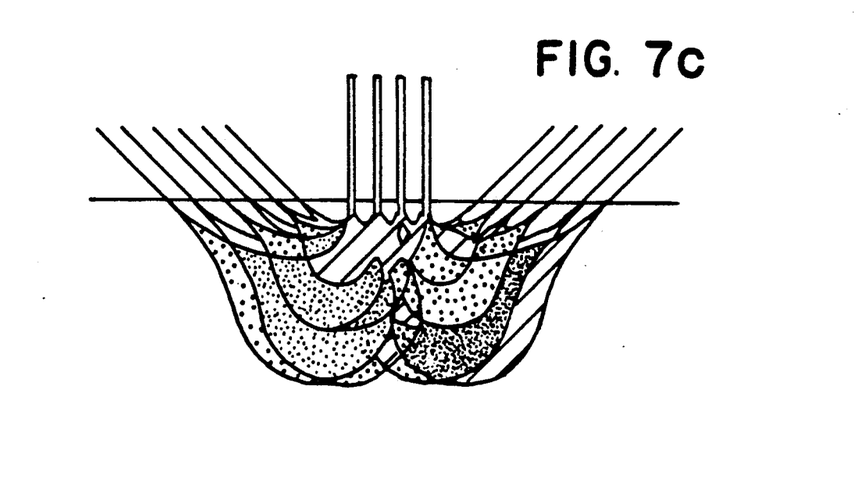
FIG. 7C is an abbreviated rendition of the image reconstruction performed by the technique of the preferred embodiment of the invention.
Figure 8:
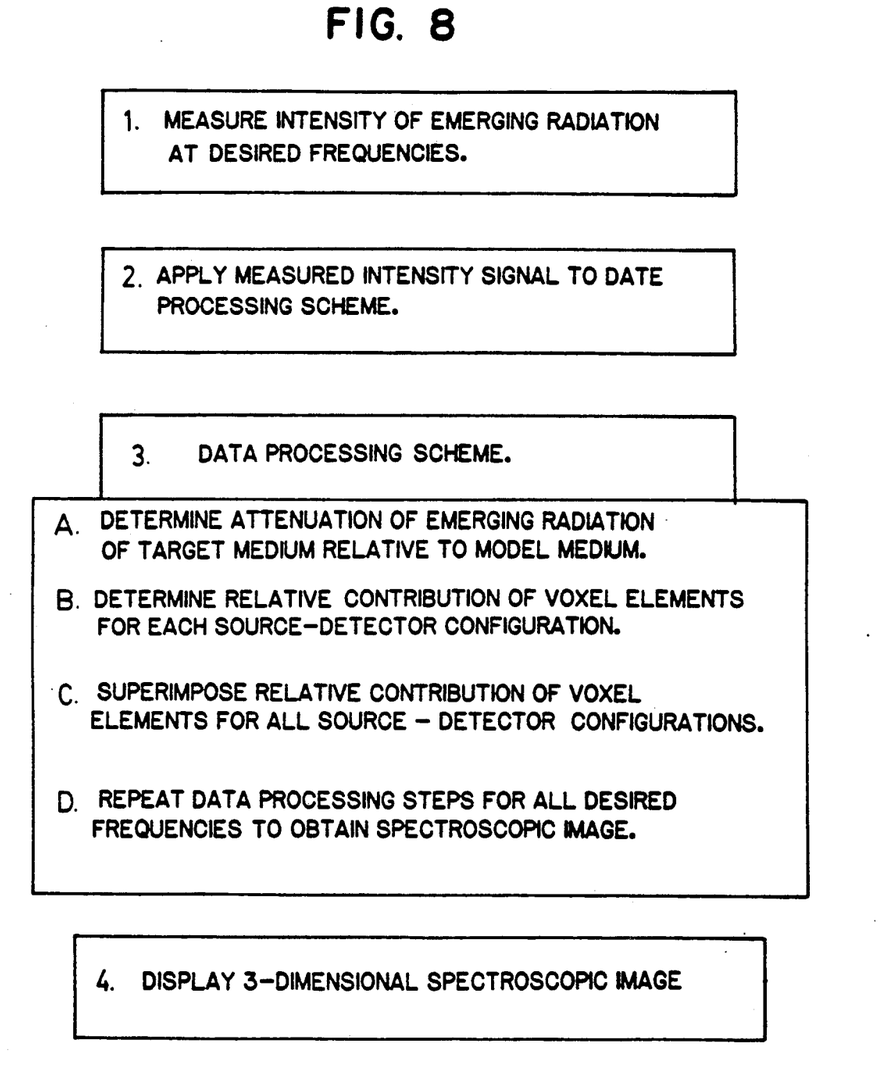
FIG. 8 is an abbreviated flow-chart of the post-receiver information processing of the method of the preferred embodiment of the present invention.

FIGS. 7 and 8 illustrate the processing of information by this preferred embodiment of the invention. The flow-chart of FIG. 8 indicates how the detected intensity information by the receiver array (indicatory numeral 6 in FIG. 6) is applied as an electrical signal to the data processing scheme.

In the data processing scheme 3 the measured intensity of emerging radiation is compared to the expected intensity thereby determining an attenuation coefficient of a corresponding scattering volume. The expected intensity is determined from calculation or actual measurements of a defined model medium as a function of position and angle of the receiver relative to the source. These calculations can be readily performed using a Monte Carlo simulation.

The intensity attenuation coefficient is then applied to a weight function to determine the relative contribution of volume elements of the target medium to the detector response for each source-detector configuration.

Image reconstruction for an unknown medium is based on weight functions calculated for a defined medium. A given location in the space of the target medium has a preferential contribution or weight to a detector response for radiation propagating in the random medium. The contribution of all points in space to the detector response is determined by calculating the product of flux through a given voxel and the probability the photons passing through this voxel will contribute to the detector response.

By this model, the effect of weak absorption in the medium on the detector response is assumed to be a linear combination of the product of the absorption cross-section and corresponding weight function for the affected voxels. A linear approximation is considered for simplicity of explanation of the preferred embodiment. However, in practice a non-linear approximation will yield a more accurate spectroscopic analysis and an image of greater resolution.

A non-linear model considers an interative scheme in which the absorption in a given voxel causes a reduction in flux through the neighboring volume elements. This scheme applies corrections to the weight functions calculated in model media to more accurately estimate the true contribution of all points in space to the detector response for the target medium.

Calculation of the weight functions can be readily performed using the Monte-Carlo method. The result yields a three-dimensional map of the relative contributions of all points in space to the detector response for a given source-detector configuration.

In practice, to the extent the values of the weight functions for a defined medium differ significantly from the actual values for the unknown medium, the resultant image will appear distorted. Provided the distortion is not too severe, recognizable optical landmarks (i.e. major vessels) can be located within the tissue. The location of these landmarks can be compared with the known anatomy (as determined, for example, by an MRI image), thereby serving as a basis for image enhancement and deconvolution.

The resolution of the images obtained will be greatest near the surface and decline in concert with the uncertainty associated with the values of the weight functions at greater depths. A 2-dimensional depiction of a relative weight function contour map of the target medium is illustrated by FIG. 7A. Therein can be seen a source 201 directed to the surface of a turbid target medium 202. The receiver 203 detects emerging radiation scattered by the medium 202. Inside the medium 202, radiation propropagating through each one of the volume elements (voxels) 204 will all contribute to the detector 203 response. The envelope 205 is a schematic illustration of a representative contour. This contour is an arbitrarily designated fraction of weight functions of those voxels contributing most to the detector response.

As depicted by the illustrations shown in FIG. 7, an image of the subsurface structure in a random medium can be obtained by calculating the product of the attenuation coefficient (as determined by comparing the measured intensity to an expected intensity from a model medium) and the corresponding weight function for each voxel for each source-detector configuration. The sum of these products corresponds to the superposition of all voxels for all source-detector configurations. This calculation, as a function of all source positions, yields a three dimensional map of the relative absorption cross-sections over all space (FIG. 7B).

The image may then be reconstructed to view a 3-dimensional depiction of the spectroscopic properties of the target medium. The spectroscopic image may be generated by comparing each of the reconstructed images obtained at each of the various frequencies. This is done using standard spectroscopic techniques.

A pictoral representation of a spectroscopic image may be seen in FIG. 7C. This reconstructed image may be displayed graphically on paper or on a video screen or any pictorial representation known in the art.

While the preferred embodiments and techniques of the invention have been presented in detail, modifications and adaptations of such techniques and embodiments will be apparent to those skilled in the art. However, it is to be expressly understood that such modifications and adaptations are within the spirit and scope of the present invention as set forth in the following claims.

I claim:

1. A method for imaging a three-dimensional target object or other optical inhomogeneity in a turbid medium, comprising the steps of:
   providing a substantially collimated beam of radiation and directing the beam onto a surface of a turbid medium containing a target object;
   providing a substantially collimated receiver to receive scattered radiation;
   performing positional scans comprising source-detector configurations having different source detector, separations and angles of the scattered radiation over the surface of the turbid medium at various separations and angles;
   applying the data obtained from each positional scan to form a three-dimensional image of the target object by:
   a. determining attenuation of emerging radiation from said target medium relative to a model medium;
   b. determining a relative contribution of volume elements for each source-detector configuration;
   c. superimposing the relative contribution of volume elements for all source-detector configurations;
   d. obtaining a spectroscopic image;
   e. displaying said spectroscopic image.

2. The method of claim 1, wherein said beam of radiation is near infrared radiation.

3. The method of claim 1, wherein said collimated receiver is a collimated receiver array.

4. The method of claim 3, wherein said receiver array includes collimated CCD detectors.

5. The method of claim 1, wherein said receiver is positioned for a reflectance measurement.

6. The method of claim 1, wherein said receiver is positioned for a transmission measurement.

7. The method of claim 1, wherein said positional scan includes having said collimated beam of radiation be laterally scanned.

8. The method of claim 1, wherein said positional scan includes a lateral translation of said collimated receiver.

9. The method of claim 1, wherein said positional scan includes an angular translation of said collimated receiver to provide differing angular information about the detector response.

10. The method of claim 1, wherein the data is applied to a data processing apparatus.

11. The method of claim 1, wherein said collimated receiver detects information regarding intensity of said scattered radiation.

12. The method of claim 1, wherein calculation of attenuation is performed by comparing measured values to expected values from a model medium calculated using Monte Carlo techniques.

13. The method of claim 12, wherein said weight function includes a calculation of a product of flux through a given voxel and an expected contribution of said voxel to a detector response.

14. The method of claim 1, wherein said attenuation step includes determining the ratio of actual data obtained from each positional scan to a calculated expected detection from said model medium.

15. The method of claim 1, wherein said determining relative contribution step includes multiplying said determined attenuation by a value of the weight function of each volume element for each source-detector configuaration under consideration.

16. The method of claim 1, wherein said superimposing step determines a three dimensional image of said target at a single frequency measurement.

17. The method of claim 1, wherein said model medium is simulated by assigning a weight to every point in the medium, wherein said weight is a product of the flux and expected contribution of a photon at a point to the detector response for a medium without an absorber.

18. The method of claim 1, wherein said imaging is used to evaluate, in situ, body tissue oxygenation state.

19. The method of claim 1, wherein said imaging is employed to measure spectroscopic properties of heme proteins, in situ.

20. The method of claim 1, wherein the substantially collimated beam of radiation is a multiple frequency beam.

21. The method of claim 20 wherein the multiple frequency beam is generated by C.W. or ultrafast pulse sources.

22. The method of claim 1, wherein steps a to c are repeated at various frequencies of radiation.

23. The method of claim 22, wherein the result of the superimposings at the various frequencies are superimposed.

* * * * *